US012642684B2

(12) United States Patent
Carlsson et al.

(10) Patent No.: US 12,642,684 B2
(45) Date of Patent: Jun. 2, 2026

(54) MONITOR DEVICE FOR OSTOMY LEAK DETECTION SYSTEM

(71) Applicant: Hollister Incorporated, Libertyville, IL (US)

(72) Inventors: Jonas P. Carlsson, Chicago, IL (US);
Anthony B. Smith, Durham, NC (US);
Christina Augustyn, Chicago, IL (US);
Ryan S. Park, Northbrook, IL (US);
Grace E. Rhinehart, Cary, NC (US)

(73) Assignee: HOLLISTER INCORPORATED,
Libertyville, IL (US)

( * ) Notice: Subject to any disclaimer, the term of this patent is extended or adjusted under 35 U.S.C. 154(b) by 736 days.

(21) Appl. No.: 18/014,422

(22) PCT Filed: Jul. 19, 2021

(86) PCT No.: PCT/US2021/070902
§ 371 (c)(1),
(2) Date: Jan. 4, 2023

(87) PCT Pub. No.: WO2022/020841
PCT Pub. Date: Jan. 27, 2022

(65) Prior Publication Data
US 2023/0240881 A1      Aug. 3, 2023

Related U.S. Application Data

(60) Provisional application No. 63/053,905, filed on Jul. 20, 2020.

(51) Int. Cl.
*A61F 5/44*          (2006.01)
*A61B 5/00*          (2006.01)

(52) U.S. Cl.
CPC .............. *A61F 5/44* (2013.01); *A61B 5/7405* (2013.01); *A61B 5/746* (2013.01)

(58) Field of Classification Search
CPC .......... A61F 5/44; A61B 5/7405; A61B 5/746
See application file for complete search history.

(56) References Cited

U.S. PATENT DOCUMENTS

| | | | |
|---|---|---|---|
| 8,398,603 B2 * | 3/2013 | Thirstrup | ............... A61B 5/746 |
| | | | 602/41 |
| 10,016,298 B2 * | 7/2018 | Thirstrup | ................ A61F 13/42 |

(Continued)

FOREIGN PATENT DOCUMENTS

| | | |
|---|---|---|
| WO | 2019/094635 A1 | 5/2019 |
| WO | 2019/120424 A1 | 6/2019 |

(Continued)

OTHER PUBLICATIONS

Office Action issued for European patent application No. EP21752479.2 dated Feb. 25, 2025, 04 pages.

(Continued)

*Primary Examiner* — Guy K Townsend
(74) *Attorney, Agent, or Firm* — Klintworth & Rozenblat LLP

(57)          ABSTRACT

An ostomy leakage detection system (10) includes a sensing accessory (12) and a monitor device (14). The sensing accessory includes sensors configured to detect ostomy effluent leakage under a skin barrier (20) of an ostomy pouch system (18). The monitor device is configured to communicate with the sensing accessory to receive ostomy effluent leakage data. The monitor device is also configured to engage with the sensing accessory and configured to be attached to the ostomy pouch system or to user's body via the sensing accessory.

9 Claims, 17 Drawing Sheets

(56) References Cited

U.S. PATENT DOCUMENTS

| | | | | |
|---|---|---|---|---|
| 10,500,084 B2 * | 12/2019 | Hansen | | A61F 5/4404 |
| 10,799,385 B2 * | 10/2020 | Hansen | | G01M 3/40 |
| 10,874,541 B2 * | 12/2020 | Seres | | G01K 3/10 |
| 10,987,243 B2 * | 4/2021 | Thirstrup | | A61B 5/746 |
| 11,096,818 B2 * | 8/2021 | Thirstrup | | A61F 13/02 |
| 11,135,084 B2 * | 10/2021 | Seres | | A61F 5/443 |
| 11,406,525 B2 * | 8/2022 | Seres | | A61B 5/4848 |
| 11,491,042 B2 * | 11/2022 | Seres | | G01F 23/261 |
| 11,504,071 B2 * | 11/2022 | Terry | | A61B 5/02055 |
| 11,534,323 B2 * | 12/2022 | Hansen | | G16H 30/40 |
| 11,547,596 B2 * | 1/2023 | Hansen | | A61F 5/44 |
| 11,559,423 B2 * | 1/2023 | Speiermann | | A61F 5/445 |
| 11,701,248 B2 * | 7/2023 | Hansen | | A61B 5/7405 604/318 |
| 11,730,622 B2 * | 8/2023 | Hansen | | A61F 5/4404 604/336 |
| 11,872,154 B2 * | 1/2024 | Speiermann | | A61B 5/150809 |
| 11,918,506 B2 * | 3/2024 | Hansen | | A61F 5/4404 |
| 11,974,938 B2 * | 5/2024 | Hansen | | A61B 5/0002 |
| 12,138,074 B2 * | 11/2024 | Hansen | | A61B 90/96 |
| 12,161,578 B2 * | 12/2024 | Carlsson | | G01M 3/16 |
| 12,161,581 B2 * | 12/2024 | Hansen | | A61F 5/448 |
| 12,178,736 B2 * | 12/2024 | Hansen | | A61F 5/44 |
| 12,178,740 B2 * | 12/2024 | Hansen | | A61F 5/4404 |
| 12,208,030 B2 * | 1/2025 | Speiermann | | A61F 5/4404 |
| 12,290,466 B2 * | 5/2025 | Hansen | | A61B 5/746 |
| 12,357,494 B2 * | 7/2025 | Fearn | | A61F 5/449 |
| 12,433,782 B2 * | 10/2025 | Hansen | | A61F 5/4404 |
| 2010/0030167 A1 | 2/2010 | Thirstrup et al. | | |
| 2015/0320585 A1 | 11/2015 | Fattman et al. | | |
| 2017/0034047 A1 | 2/2017 | Bhattacharya et al. | | |
| 2017/0340474 A1 * | 11/2017 | Thirstrup | | A61B 5/746 |
| 2019/0037437 A1 | 1/2019 | Sun et al. | | |
| 2019/0133812 A1 * | 5/2019 | Seres | | A61F 5/443 |
| 2019/0142623 A1 | 5/2019 | Norman et al. | | |
| 2019/0240059 A1 | 8/2019 | Michael et al. | | |
| 2019/0374372 A1 * | 12/2019 | Seres | | A61B 5/6802 |
| 2020/0000624 A1 * | 1/2020 | Gibbons | | A61B 5/444 |
| 2020/0246174 A1 * | 8/2020 | Hansen | | A61F 5/443 |
| 2020/0246175 A1 * | 8/2020 | Hansen | | A61F 5/4404 |
| 2020/0246176 A1 * | 8/2020 | Hansen | | A61F 5/445 |
| 2020/0246177 A1 | 8/2020 | Ask et al. | | |
| 2020/0375784 A1 * | 12/2020 | Hansen | | A61F 5/443 |
| 2020/0375785 A1 * | 12/2020 | Hansen | | A61B 90/361 |
| 2020/0390587 A1 * | 12/2020 | Svanegaard | | G16H 40/40 |
| 2020/0395120 A1 * | 12/2020 | Svanegaard | | A61F 5/4404 |
| 2020/0405230 A1 * | 12/2020 | Svanegaard | | A61B 5/6813 |
| 2021/0000414 A1 * | 1/2021 | Svanegaard | | A61F 5/4404 |
| 2021/0007663 A1 * | 1/2021 | Svanegaard | | G16H 40/40 |
| 2021/0007881 A1 * | 1/2021 | Svanegaard | | A61F 5/4404 |
| 2021/0059603 A1 * | 3/2021 | Svanegaard | | A61B 5/4851 |
| 2021/0275341 A1 | 9/2021 | Kristoffer | | |
| 2021/0353448 A1 | 11/2021 | George et al. | | |
| 2021/0369491 A1 | 12/2021 | Holden | | |
| 2022/0031495 A1 * | 2/2022 | Seres | | A61B 5/002 |
| 2022/0117771 A1 * | 4/2022 | Fearn | | A61F 5/445 |
| 2022/0257405 A1 | 8/2022 | Peder et al. | | |
| 2022/0265457 A1 * | 8/2022 | Emborg | | A61F 5/448 |
| 2022/0313473 A1 * | 10/2022 | Schertiger | | A61F 5/4404 |
| 2022/0378602 A1 * | 12/2022 | Hansen | | A61F 5/4404 |
| 2023/0030622 A1 * | 2/2023 | Nielsen | | A61F 5/443 |
| 2023/0031979 A1 | 2/2023 | Stendevad et al. | | |

FOREIGN PATENT DOCUMENTS

| | | | |
|---|---|---|---|
| WO | 2019/120425 A1 | 6/2019 | |
| WO | 2019/120426 A1 | 6/2019 | |
| WO | 2019/120427 A1 | 6/2019 | |
| WO | 2019/120428 A1 | 6/2019 | |
| WO | 2019/120429 A1 | 6/2019 | |
| WO | 2019/120430 A1 | 6/2019 | |
| WO | 2019/120432 A1 | 6/2019 | |
| WO | 2019/120433 A1 | 6/2019 | |
| WO | 2019/120434 A1 | 6/2019 | |
| WO | 2019/120435 A1 | 6/2019 | |
| WO | 2019/120436 A1 | 6/2019 | |
| WO | 2019/120437 A1 | 6/2019 | |
| WO | 2019/120440 A1 | 6/2019 | |
| WO | 2019/120441 A1 | 6/2019 | |
| WO | 2019/120442 A1 | 6/2019 | |
| WO | 2019/120443 A1 | 6/2019 | |
| WO | 2019/120444 A1 | 6/2019 | |
| WO | 2019/120445 A1 | 6/2019 | |
| WO | 2019/120446 A1 | 6/2019 | |
| WO | 2019/120448 A1 | 6/2019 | |
| WO | 2019/120449 A1 | 6/2019 | |
| WO | 2019/120450 A1 | 6/2019 | |
| WO | 2019/120451 A1 | 6/2019 | |
| WO | 2019/120452 A1 | 6/2019 | |
| WO | 2019/120453 A1 | 6/2019 | |
| WO | 2019/120458 A1 | 6/2019 | |
| WO | 2019/149330 A1 | 8/2019 | |
| WO | 2019/161859 A1 | 8/2019 | |
| WO | 2019/161860 A1 | 8/2019 | |
| WO | 2019/161861 A1 | 8/2019 | |
| WO | 2019/161863 A1 | 8/2019 | |
| WO | WO-2019161862 A1 * | 8/2019 | ............ A61F 5/445 |
| WO | 2019/169327 A1 | 9/2019 | |
| WO | 2019/174687 A1 | 9/2019 | |
| WO | 2019/174692 A1 | 9/2019 | |
| WO | 2019/174693 A1 | 9/2019 | |
| WO | 2019/174694 A1 | 9/2019 | |
| WO | 2019/174695 A1 | 9/2019 | |
| WO | 2019/174696 A1 | 9/2019 | |
| WO | 2019/174697 A1 | 9/2019 | |
| WO | 2019/174698 A1 | 9/2019 | |
| WO | 2019/174699 A1 | 9/2019 | |
| WO | 2019/238180 A1 | 12/2019 | |
| WO | 2019/238181 A1 | 12/2019 | |
| WO | 2019/238182 A1 | 12/2019 | |
| WO | 2019/238183 A1 | 12/2019 | |
| WO | 2020/035121 A1 | 2/2020 | |
| WO | WO-2020076609 A1 * | 4/2020 | ............ A61F 5/445 |
| WO | 2020/123771 A2 | 6/2020 | |
| WO | 2020/156624 A1 | 8/2020 | |
| WO | 2020/156625 A1 | 8/2020 | |
| WO | 2020/156626 A1 | 8/2020 | |
| WO | 2020/169162 A1 | 8/2020 | |
| WO | 2020/173534 A1 | 9/2020 | |
| WO | 2020/216426 A1 | 10/2020 | |
| WO | 2020/216427 A1 | 10/2020 | |
| WO | 2020/216429 A1 | 10/2020 | |
| WO | 2020/259775 A1 | 12/2020 | |
| WO | 2021/063463 A1 | 4/2021 | |
| WO | 2021/063466 A1 | 4/2021 | |
| WO | 2021/165703 A1 | 8/2021 | |
| WO | 2021/165705 A1 | 8/2021 | |
| WO | 2021/185425 A1 | 9/2021 | |
| WO | 2021/209104 A1 | 10/2021 | |
| WO | 2022/063379 A1 | 3/2022 | |
| WO | 2022/078561 A1 | 4/2022 | |
| WO | 2022/207049 A1 | 10/2022 | |

OTHER PUBLICATIONS

International Search Report issued Dec. 13, 2021 by ISA/EPO in connection with PCT/US2021/070902.

Written Opinion issued Dec. 13, 2021 by ISA/EPO in connection with PCT/US2021/070902.

International Preliminary Report on Patentability issued Feb. 2, 2023 by WIPO in connection with PCT/US2021/070902.

Invitation to Pay Additional Fees issued Oct. 20, 2021 by ISA/EPO in connection with PCT/US2021/070902.

Australian Office Action issued in connection with AU application No. 2021311847 dated Mar. 26, 2026, 05 pages.

* cited by examiner

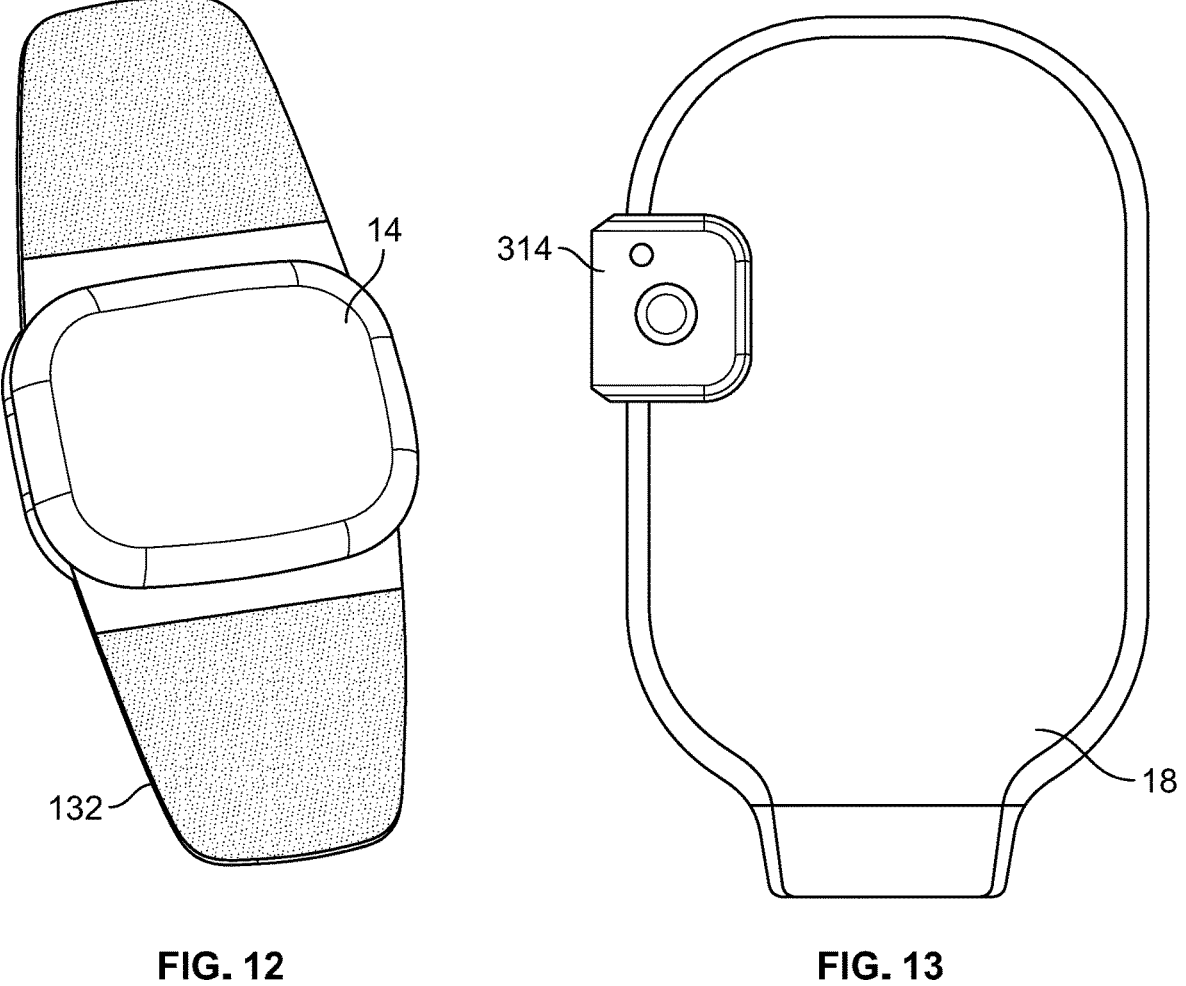
FIG. 12                    FIG. 13

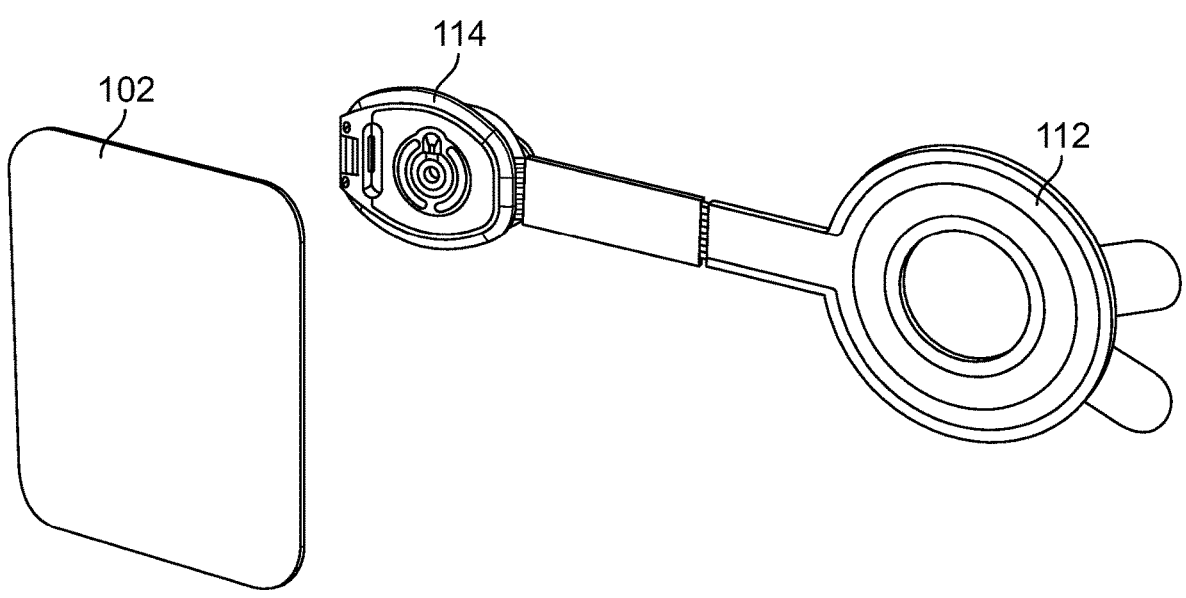
FIG. 19
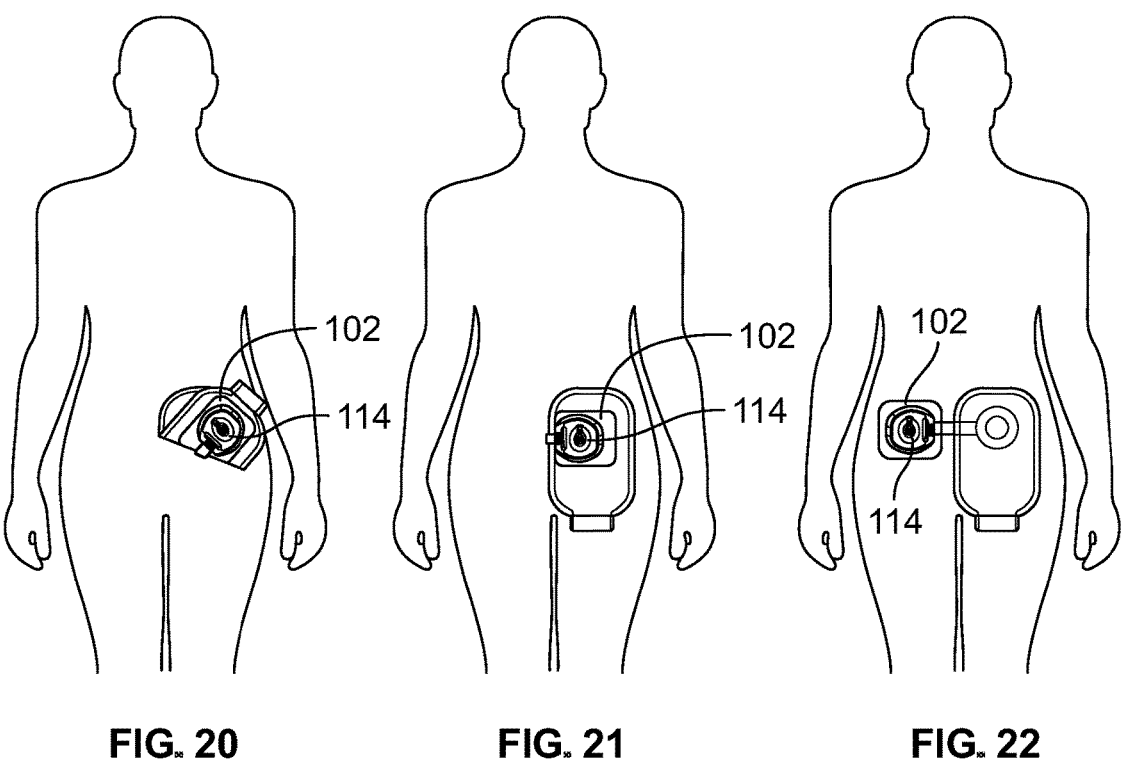
FIG. 20          FIG. 21          FIG. 22

Lift top while squeezing sides

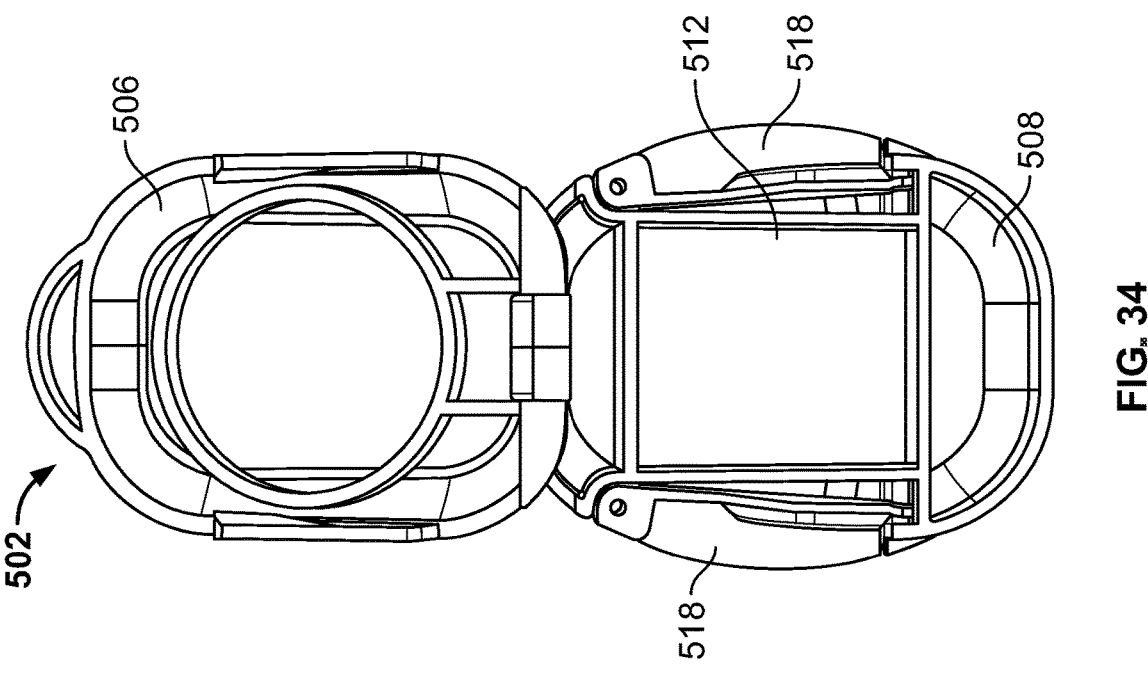
FIG. 34
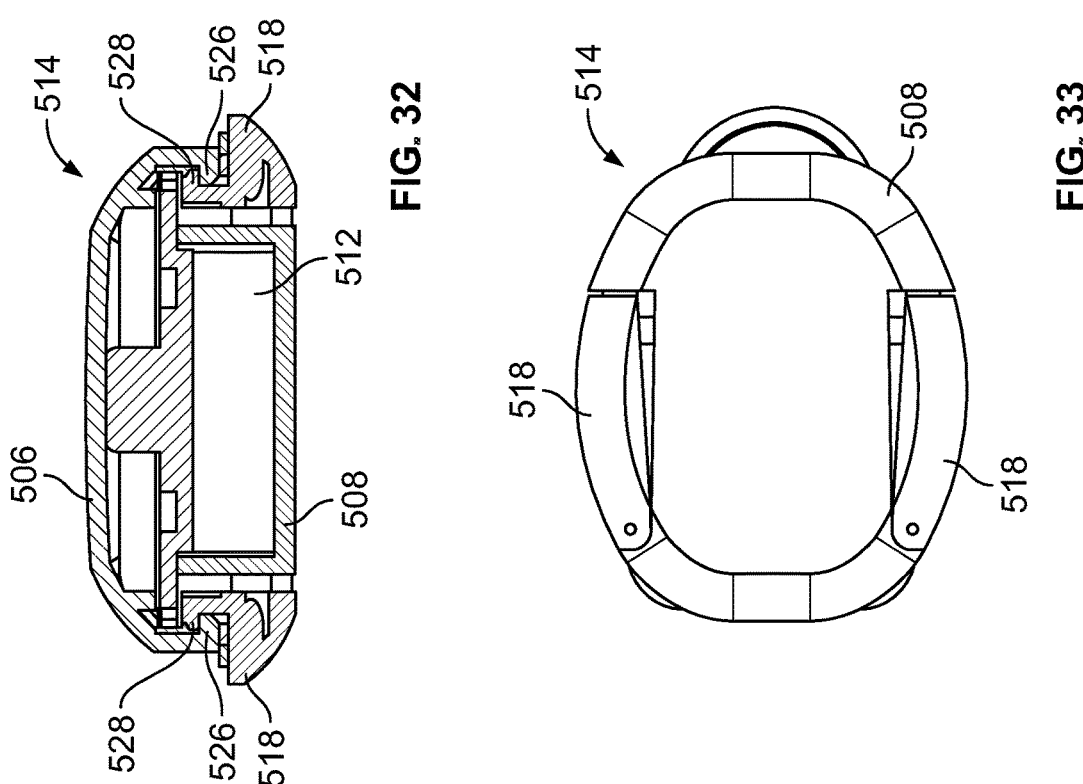
FIG. 32
FIG. 33

MONITOR DEVICE FOR OSTOMY LEAK DETECTION SYSTEM

This is a National Stage Application of International Patent Application No. PCT/US2021/070902 filed Jul. 19, 2021, which claims the benefit of and priority to U.S. Provisional Application No. 63/053,905 filed Jul. 20, 2020, the entirety of which are incorporated fully herein by reference.

BACKGROUND

The following description relates generally to a leakage detection system for medical devices, and more particularly to a monitor device for detecting leakage in ostomy appliances.

An ostomy pouch system typically includes a pouch formed from opposing sidewalls defining an internal collection area, an inlet opening for receiving a stoma, and an ostomy appliance for attaching the pouch to a user. The ostomy appliance may include, for example, an ostomy barrier of a one-piece pouch system, which is attached to one of the pouch sidewalls proximate an inlet opening, a faceplate for a two-piece pouch system configured to releasably engage a pouch, and a barrier ring. The ostomy appliance may include a skin barrier material for adhering to and sealing against user's peristomal skin surrounding the stoma.

The ostomy appliance may be susceptible to ostomy effluent leakage, and the seal formed between the skin barrier material and the user may weaken. Often, the user may be unaware of or cannot easily assess an extent of weakening in the seal. Thus, the user may not become aware of a weakened seal, and consequently, the ostomy effluent may leak through to an exterior of the ostomy appliance.

Accordingly, it is desirable to provide a leakage detection system for ostomy appliances.

SUMMARY

In one aspect, an ostomy leakage detection system including a sensing accessory and a monitor device is provided. The sensing accessory may comprise sensors configured to detect ostomy effluent leakage under a skin barrier of an ostomy pouch system. The monitor device may be configured to communicate with the sensing accessory to receive ostomy effluent leakage data. The monitor device may also be configured to engage with the sensing accessory and configured to be attached to the ostomy pouch system or to user's body via the sensing accessory.

In an embodiment, the monitor device may be attached to a body-side surface of the ostomy pouch system. In another embodiment, the monitor device may be attached to a distal surface of the ostomy pouch system. In such embodiments, the sensing accessory may include a first alignment member and the monitor device may include a second alignment member, wherein the sensing accessory and the monitor device are engaged with each other by aligning the first and second alignment members.

In an embodiment, the sensing accessory may include an attachment portion comprising an adhesive, wherein the monitor device is attached to the ostomy pouch system via the attachment portion. In another embodiment, the sensing accessory may include an attachment portion comprising a hook member or a loop member, wherein the monitor device is attached to the ostomy pouch system by engaging the hook member or the loop member of the attachment portion to a corresponding hook or loop member provided on the ostomy pouch system. In some embodiments, the monitor device may be releasably coupled to the sensing accessory, such that the monitor device can be removed after the attachment portion is attached to the ostomy pouch system.

In an embodiment, the monitor device may be magnetically clipped to the ostomy pouch system.

In another embodiment, the sensing accessory may include an attachment portion comprising an adhesive, wherein the monitor device is attached to the user's body via the attachment portion. In yet another embodiment, the monitor device may be attached to the ostomy pouch system or user's body via an adhesive member provided on a body-facing surface of the monitor device.

In an embodiment, the monitor device may be attached to the ostomy pouch system or user's body via an adhesive patch separately provided from the monitor device or a pocket configured to hold the monitor device.

In another aspect, a monitor device for an ostomy leakage detection system may comprise electronics, a casing for housing the electronics, and an alignment member. The electronics may be configured to communicate with a sensing accessory or an ostomy barrier comprising leakage detection sensors to receive signals for detecting an ostomy effluent leakage. The alignment member may be configured to engage with a mating alignment member provided in the sensing accessory or the ostomy barrier to facilitate attachment of the monitor device to the sensing accessory or the ostomy barrier.

In an embodiment, the casing may be a hinged casing comprising a top casing and a bottom casing. The monitor device may further comprise side clasps and a top clasp and configured to be opened by squeezing the side claps and lifting the top clasp. The top clasp may be provided in the top casing and the side claps may be arranged in or attached to the bottom casing.

In an embodiment, the monitor device may include a squeeze release device comprising the side clasps, a spring connecting the side claps, and a pair of latches, wherein the pair of latches may be configured to engage a pair of catches provided on the top casing. The monitor device may further include an electronics housing, wherein the squeeze release device may be arranged in the bottom casing and the electronics housing containing the electronics may be arranged over the squeeze release device. In another embodiment, the top casing may include a pair of latches and the each of the side claps may include a catch configured to engage with one of the latches. The side claps may be attached to the bottom casing with a spring arranged between each of the side claps and the bottom casing such that the side clasps can be squeezed toward the bottom casing. In such embodiments, the monitor device may be configured such that the latches and the catches are engaged with each other in a closed position, and the latches may be released from the catches when the side claps are squeezed. In some embodiments, the monitor device may further include a board seal configured to cover and protect the electronics from humidity and external environment.

The monitor device of any of the foregoing embodiments may further comprise a plurality of conductive members configured to contact a plurality of connection points of the sensing accessory or the ostomy barrier to electrically connect the monitor device to the sensing accessory or the ostomy barrier.

In an embodiment, the alignment member may include a center raised key member and a peripheral raised member, wherein the center raised key member may be provided generally in a center of the bottom casing and the peripheral raised member is arranged proximate a hinge of the casing. In such an embodiment, the mating alignment member may include a center key opening configured to receive the center raised key member and a peripheral opening configured to receive the peripheral raised member.

In another embodiment, the alignment member may include first and second raised members, and the mating alignment member may include a first opening configured to receive the first raised member and a second opening configured to receive the second raised member. In such an embodiment, the plurality of conductive members may be arranged between the first and second raised members.

Other objects, features, and advantages of the disclosure will be apparent from the following description, taken in conjunction with the accompanying sheets of drawings, wherein like numerals refer to like parts, elements, components, steps, and processes.

BRIEF DESCRIPTION OF THE DRAWINGS

FIG. 12 is an illustration of a monitor device coupled to an intermediate component including a hook or a loop fastener for attaching the monitor device to an ostomy pouch according to an embodiment;

FIG. 13 is an illustration of a monitor device magnetically clipped onto an ostomy pouch system according to another embodiment;

FIG. 19 is a perspective illustration of the monitor device and the sensing accessory of FIG. 18 and an adhesive patch for attaching the monitor device to a user or an ostomy pouch according to an embodiment;

FIG. 20 is an illustration of a monitor device attached to a body-side of an ostomy pouch according to an embodiment;

FIG. 21 is an illustration of a monitor device attached to a distal-side of an ostomy pouch according an embodiment;

FIG. 22 is an illustration of a monitor device attached to a user according to an embodiment;

FIGS. 30-34 are various views of a monitor device according to another embodiment;

DETAILED DESCRIPTION

Figure 1:
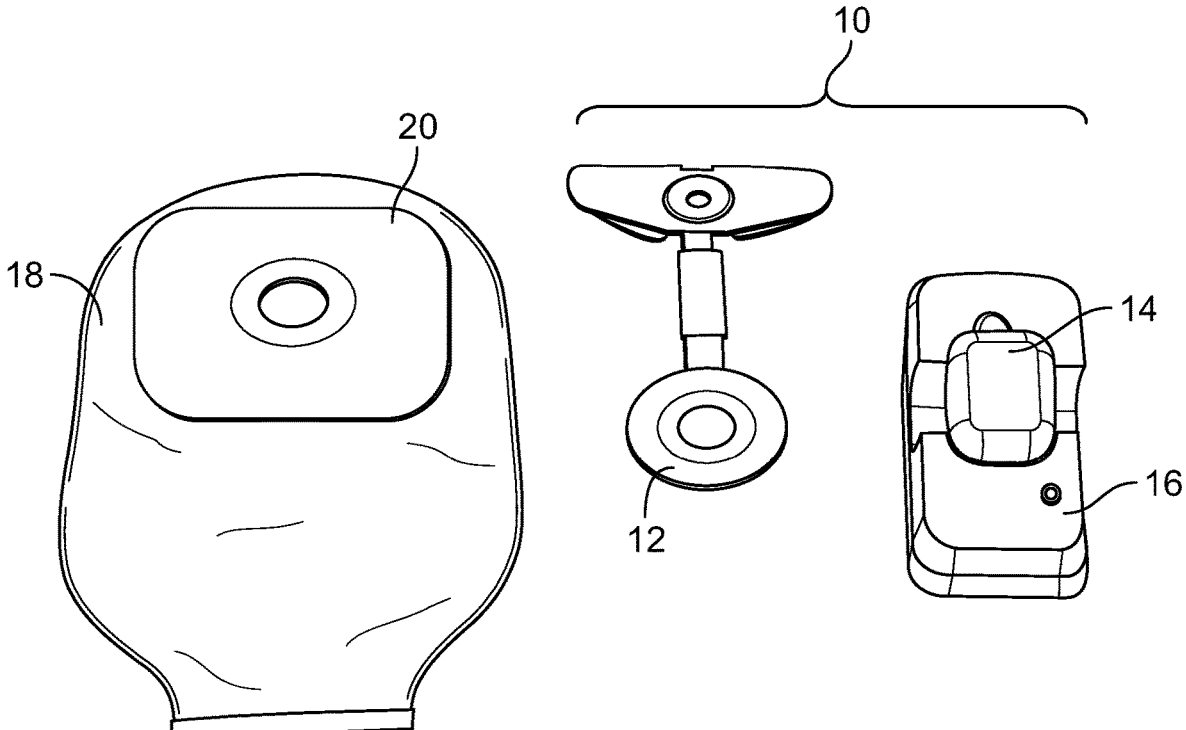
FIG. 1 is a plan view of an ostomy leak detection system and a one-piece pouch system according to an embodiment.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

FIG. 1 shows an ostomy leakage detection system 10 according to an embodiment. The ostomy leak detection system 10 may be configured to detect ostomy effluent leakage under a skin barrier and alert a user. The ostomy leakage detection system 10 may generally comprise a sensing accessory 12, a wearable subsystem 14, which is also referred to herein as a "monitor device", a charging dock 16, and a mobile application (not shown). The sensing accessory 12 may be provided as an ostomy accessory configured to be attached to a skin barrier of an ostomy appliance, for example, an ostomy barrier of a one-piece pouch system or a faceplate for a two-piece pouch system. A one-piece ostomy pouch system 18 comprising an ostomy barrier 20 according to an embodiment is shown in FIG. 1.

The wearable subsystem 14 may be configured to communicate with the sensing accessory 12 comprising sensors configured to detect ostomy effluent leakage. The wearable subsystem 14 may be secured to an ostomy pouch system or to a user. In an embodiment, the wearable subsystem 14 may be attached to an ostomy pouch system or to a user via an intermediate component, such as the sensing accessory 12, wherein the wearable subsystem 14 may be coupled to the intermediate component which is then secured to the ostomy pouch system or the user. The intermediate component may be attached to the ostomy pouch system via an adhesive, hook and loop fasteners, or the like. The wearable subsystem 14 may be attached to the intermediate component through a means of friction through a spring or mechanical clip, mechanical interlock, adhesive, hook and loop fasteners, magnetic force, or a combination of thereof.

In an embodiment, the wearable subsystem 14 may comprise an adhesive member for adhering the wearable subsystem 14 to a component or components of an ostomy system. The adhesive member may be configured as a removable member that can be removed from the wearable subsystem 14 and may be replaced with a new adhesive member for reapplication to the same ostomy system component or to a new ostomy system component. In another embodiment, the wearable subsystem 14 may comprise a hook fastener member or a loop fastener member which is configured to mate with a hook or loop member arranged on an ostomy system component.

In an embodiment, the wearable subsystem may comprise a clamping device configured to slide onto a component of an ostomy system and held in place by friction. A clamping portion of the clamping device may be configured as a flexible component of the wearable subsystem or may comprise mechanical springs to provide a spring clamping force. The clamping device may be configured as a hinge or slide, wherein a movable non-spring component is moved into a place to allow clamping onto a component of an ostomy system. When the wearable subsystem is arranged at a target location, a screw, cam, wedge, or other similar mechanism may be used to fix the moveable component of the clamping device in place.

In an embodiment, the wearable subsystem 14 may be configured to engage with the sensing accessory 12 to make a direct electrical connection for communication therethrough. In some embodiments, the wearable subsystem 14 may be configured to communicate with the sensing accessory 12 wirelessly. The sensing accessory 12 may be configured to communicate leakage detection signals to the wearable subsystem 14. In an embodiment, the wearable subsystem 14 may be configured to perform at least some processing of the leakage detection signals and send an alert to a user.

The wearable subsystem 14 may also be configured to communicate wirelessly with the mobile application. The mobile application may be a digital subsystem housed on a mobile device of a user. The mobile application may be configured to process leak detection data and to provide an alert or other information about the leak detection system to the user. The charging dock 16 may be configured to recharge the wearable subsystem 14 and to communicate with the wearable subsystem 14 and alert the user, for example when the system is in use at night.

Figures 2, 3:
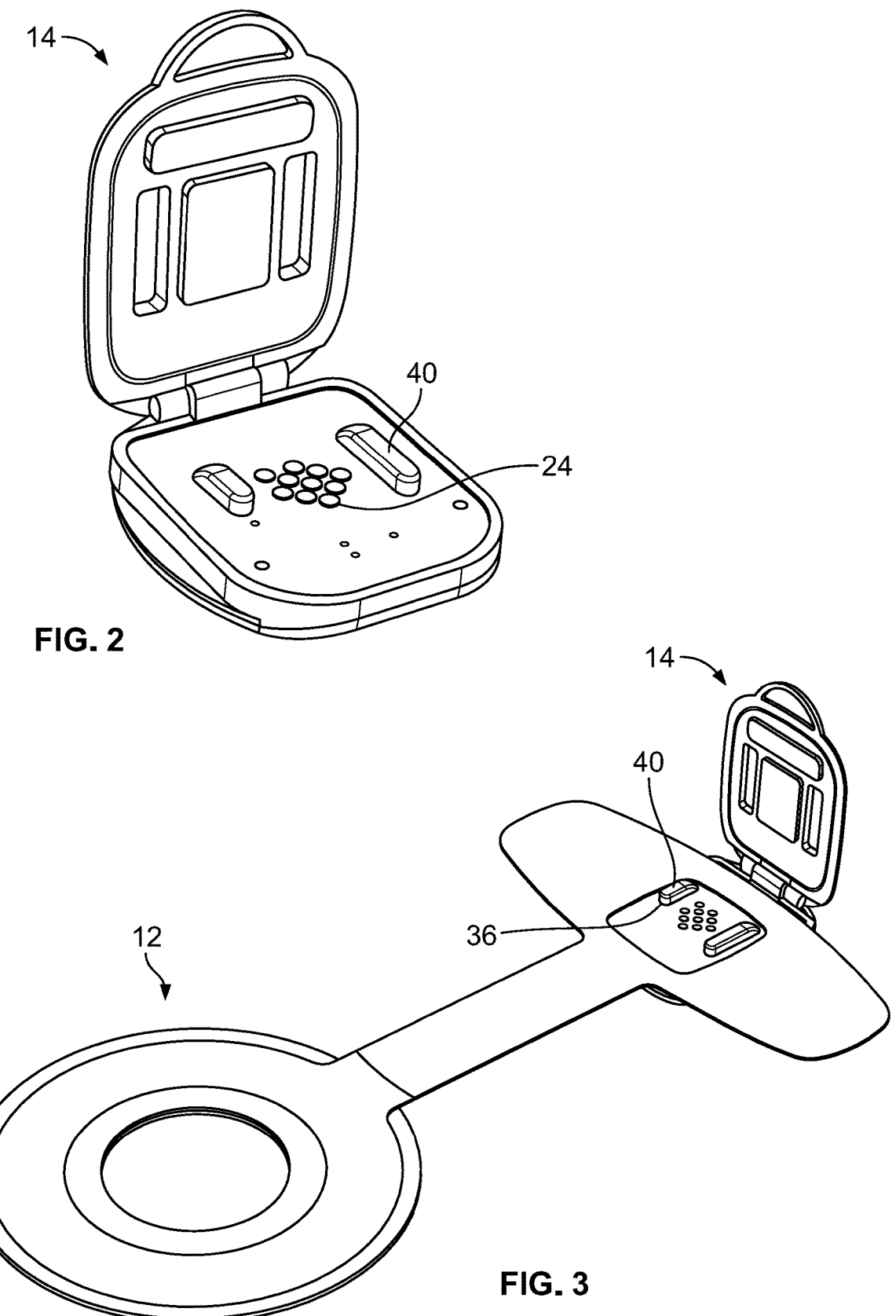
FIG. 2 is an illustration of a monitor device according to an embodiment.
FIG. 3 is an illustration of the monitor device of FIG. 2 engaged with a sensing accessory according to an embodiment.

The wearable subsystem 14 according to an embodiment is shown in FIG. 2. The wearable subsystem 14 may comprise a hinged casing, an imbedded circuit board, a battery, and a motor. The casing may include alignment features 22 that correspond to alignment features of the sensing accessory 12. The circuit board may include raised conductive pads 24 configured to contact terminal ends of sensing traces of the sensing accessory 12. The circuit board may also include components to analyze signals received from the sensing accessory 12, communicate with a mobile device or the charging dock 16, and alert a user. The user may form a connection between the sensing accessory 12 and the wearable subsystem 14 by aligning the corresponding alignment features 22 as shown in FIG. 3 and closing the wearable subsystem 14. In an embodiment, the wearable subsystem 14 may be configured to function as a relay from the sensing accessory 12 to the user and the other parts of the leak detection system 10. The wearable subsystem 12 may be configured to physically and electronically couple to the sensing accessory 12 and analyze signals coming therefrom.

Figure 4:
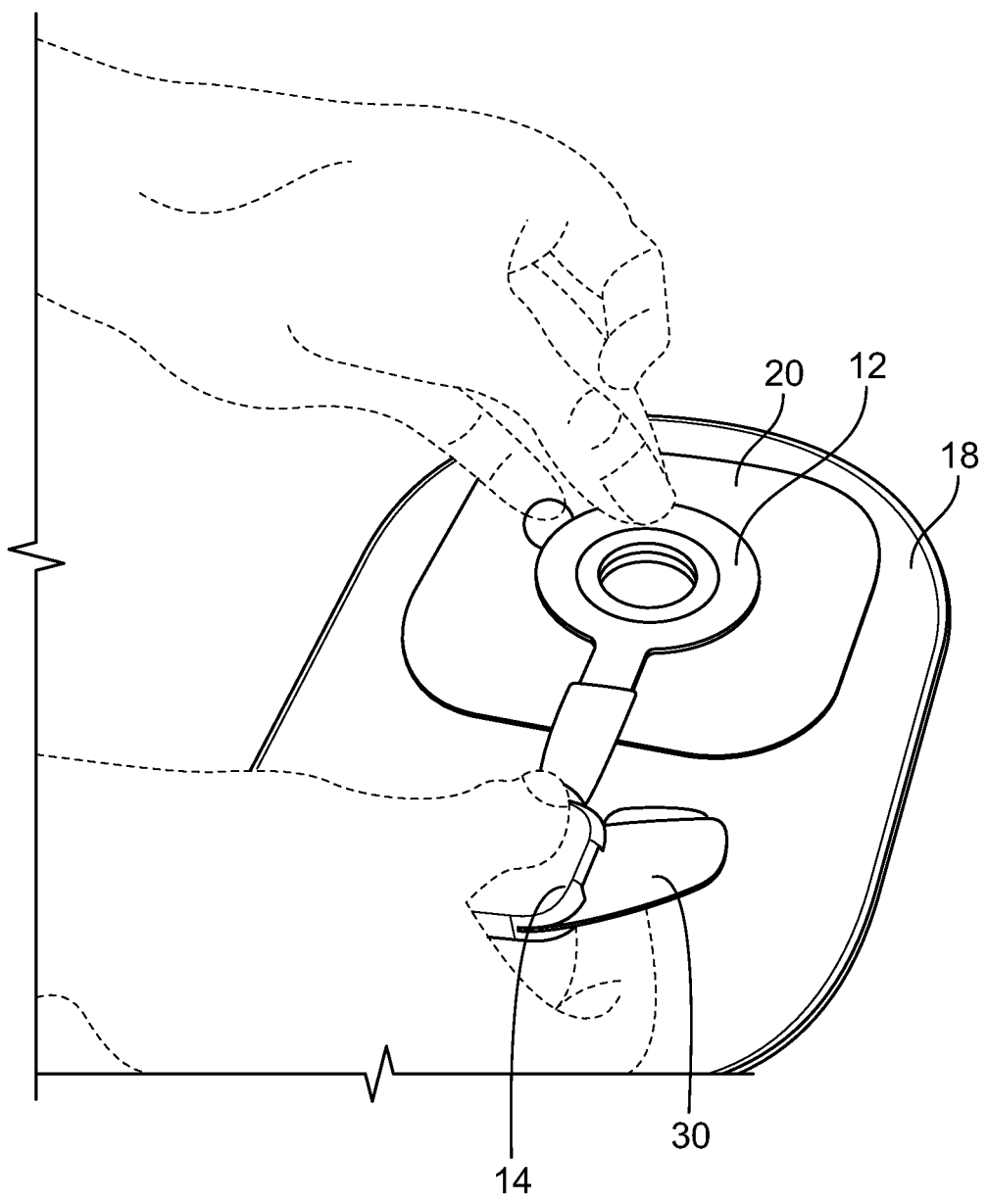
FIG. 4 is an illustration of a sensing accessory attached to an ostomy skin barrier and coupled to a monitor device according to an embodiment.
Figure 5:
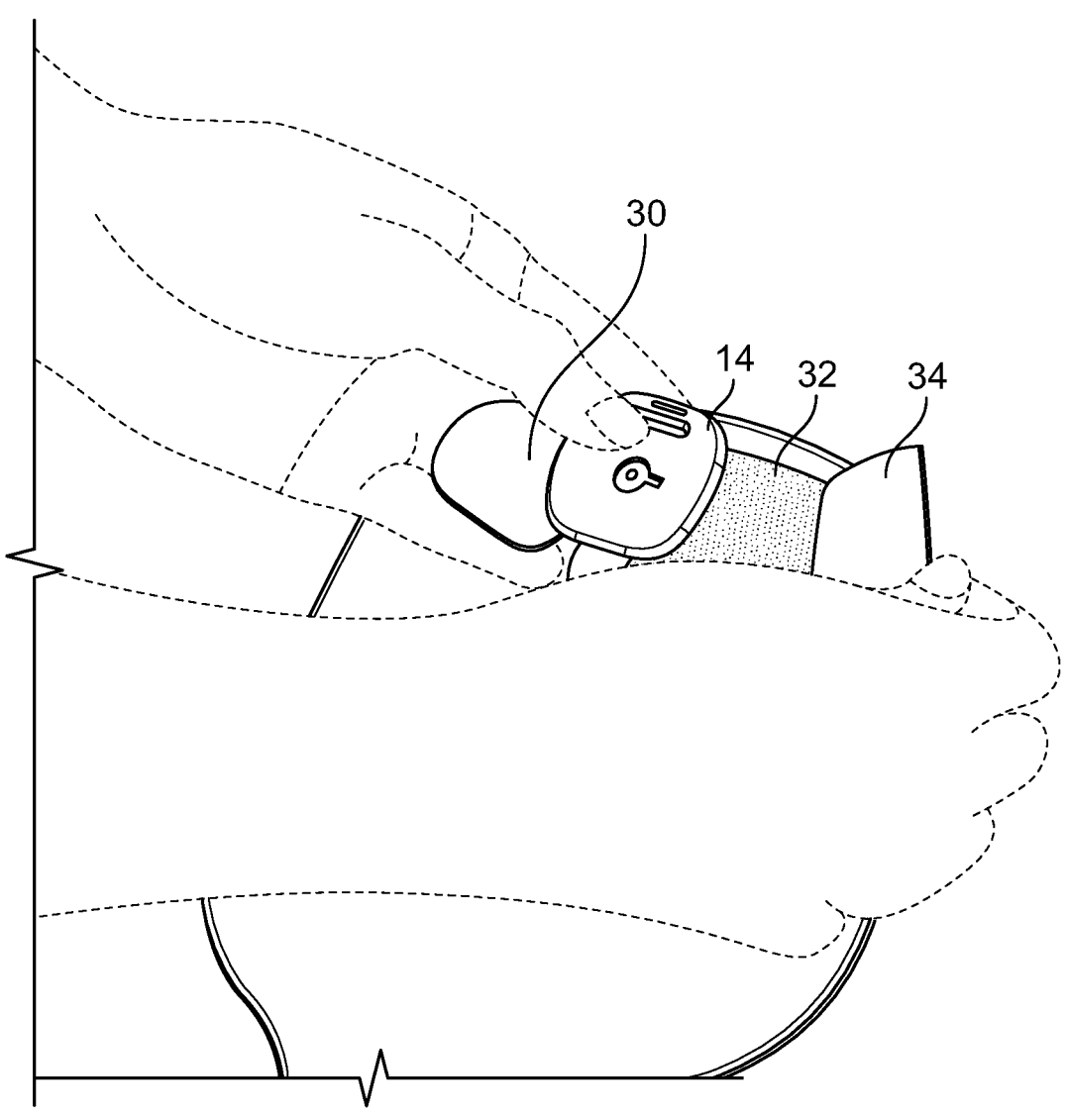
FIG. 5 is an illustration of a user removing a release liner from an attachment portion of the sensing accessory of FIG. 4 before attaching the monitor device to an ostomy pouch according to an embodiment.

In an embodiment, the sensing accessory 12 with the wearable subsystem 14 coupled thereto may be attached to a skin barrier, such as the ostomy barrier 20 of the one-piece ostomy pouch system 18 as shown in FIG. 4. The sensing accessory 12 may comprise a wing-like attachment portion 30 including an adhesive 32 provided on a pouch facing surface and release liners 34 covering the adhesives 32 as best shown in FIG. 5. A user may remove the release liners 34 before attaching the wing-like attachment portion 30 to an ostomy pouch system or to user's skin. In another embodiment, the attachment portion may comprise a hook member 132 or a loop member configured to mate with a hook or loop member (not shown) provided on an ostomy pouch system to attach the wearable subsystem 14 to the ostomy pouch system as shown in FIG. 12.

Figure 6:
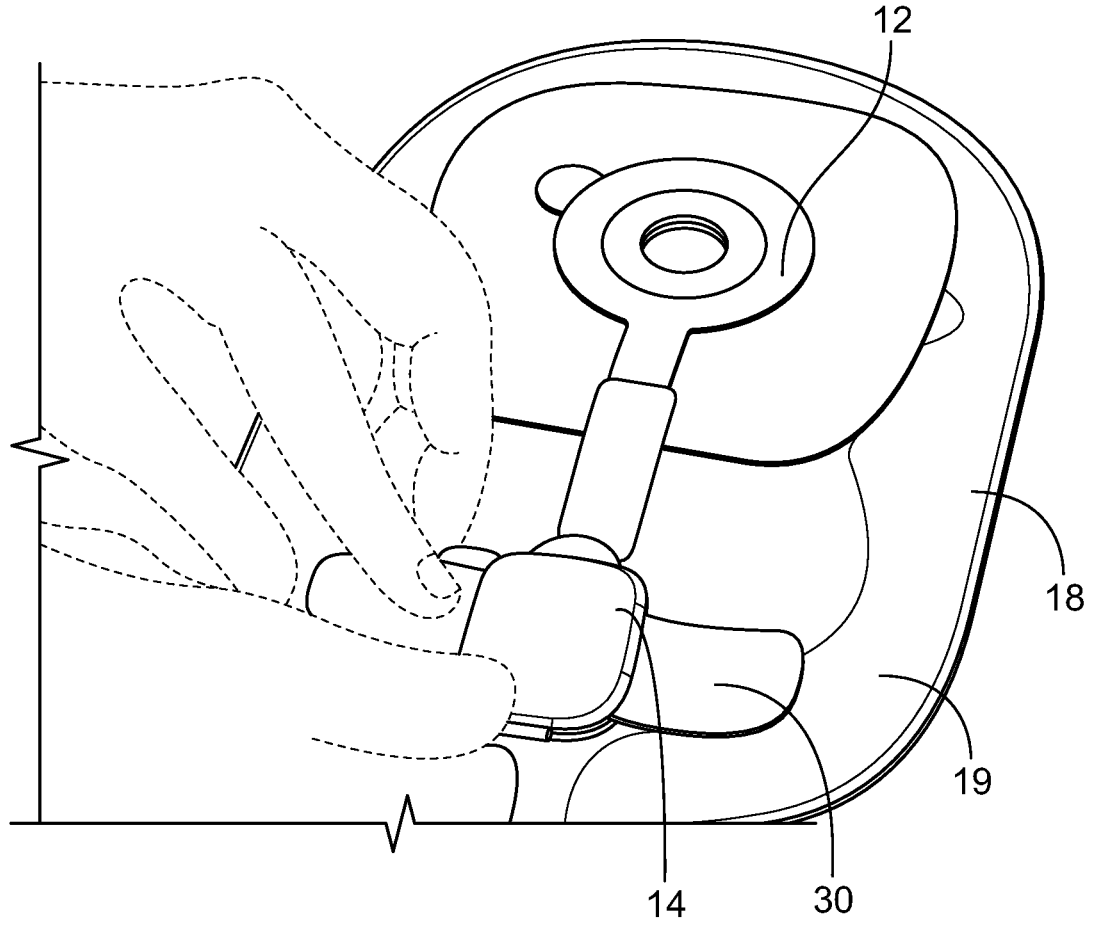
FIG. 6 is an illustration of the monitor device of FIG. 4 attached to a body-side surface of the ostomy pouch according to an embodiment.
Figure 7:
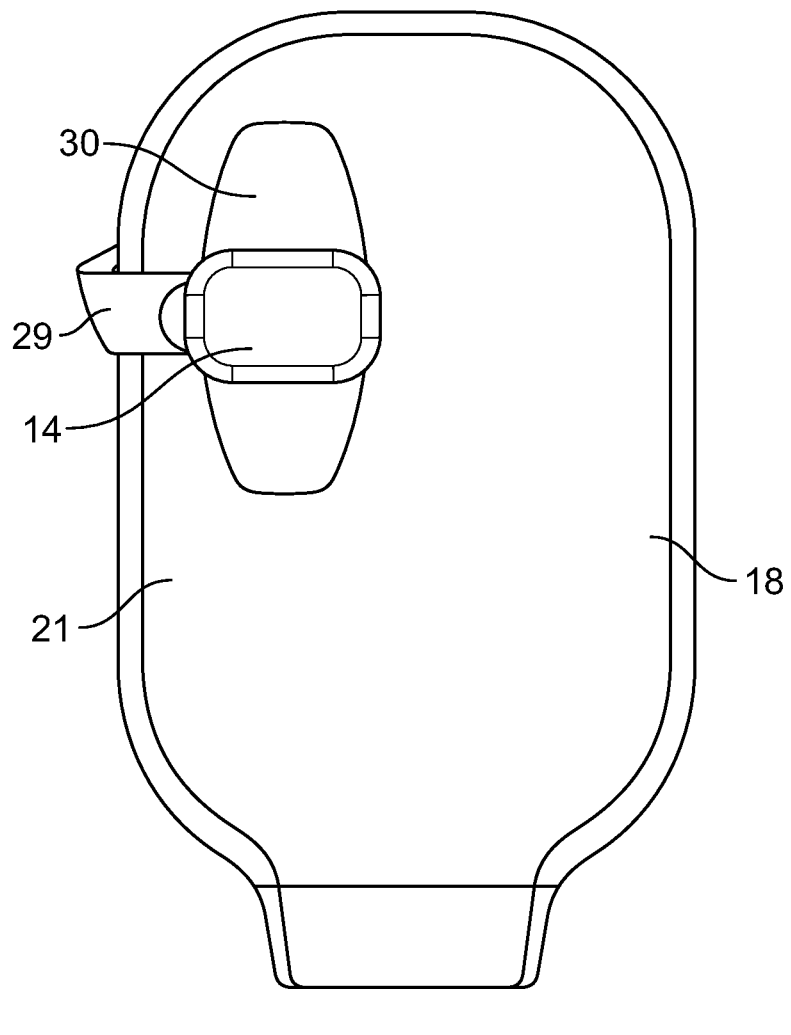
FIG. 7 is an illustration of a monitor device attached to a distal surface of an ostomy pouch according to another embodiment.
Figures 8, 9, 10, 11:
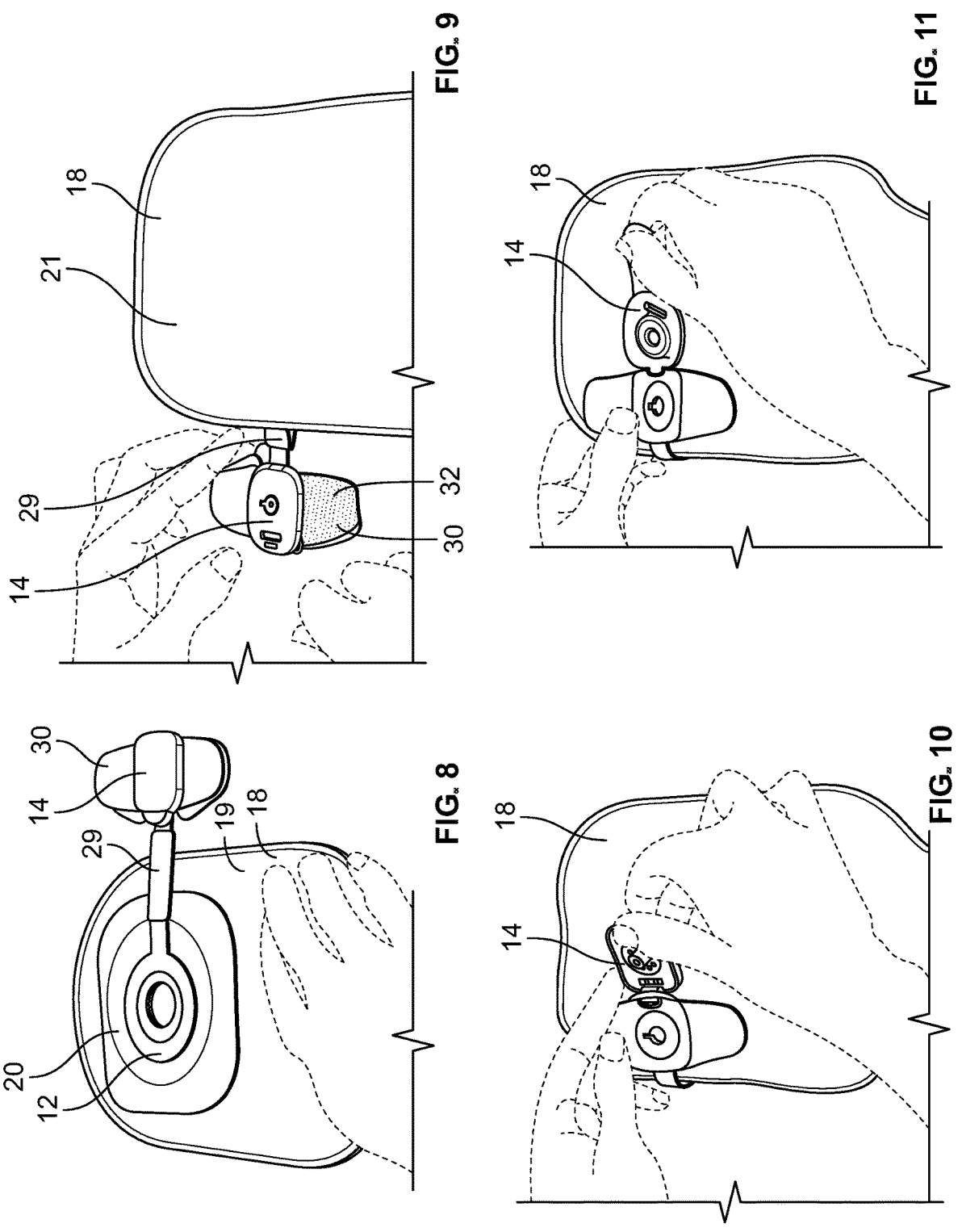
FIG. 8 is an illustration of a body-side view of the ostomy pouch of FIG. 7 before the monitor device is attached to the distal surface of the ostomy pouch according to an embodiment.
FIG. 9 is an illustration of a distal-side view of the ostomy pouch system of FIG. 8.
FIGS. 10 and 11 are illustrations of a user removing the monitor device of FIG. 7 from the sensing accessory according to an embodiment.

In an embodiment, the wearable subsystem 14 may be coupled to the sensing accessory 12 and attached to a body-side surface 19 of the ostomy pouch system 18 via the attachment portion 30 as shown in FIG. 6. In another embodiment, the wearable subsystem 14 may be coupled to the sensing accessory 12 and attached to a distal surface 21 of the ostomy pouch system 18 via the attachment portion 30 as shown in FIG. 7. In such an embodiment, the sensing accessory 12 may be attached to the skin barrier 20, such that the attachment portion 30 may extend to one side of the ostomy pouch system 18 as shown in FIGS. 8 and 9. The sensing accessory 12 may be configured such that the attachment portion 30 and the wearable subsystem 14 coupled thereto may extend beyond a peripheral edge of the ostomy pouch system 18 and a tail portion 29 of the sensing accessory 12 may be folded over to secure the wearable subsystem 14 to the distal surface 21 of the ostomy pouch system 18 as shown in FIGS. 7-9. The wearable subsystem 14 may be releasably coupled to the sensing accessory 12, such that the wearable subsystem 14 may be removed before changing the ostomy pouch system 18 as shown in FIGS. 10 and 11.

A monitor device 314 according to another embodiment is shown in FIG. 13. The monitor device 314 may be configured to magnetically clip onto the ostomy pouch system 18.

Figure 15:
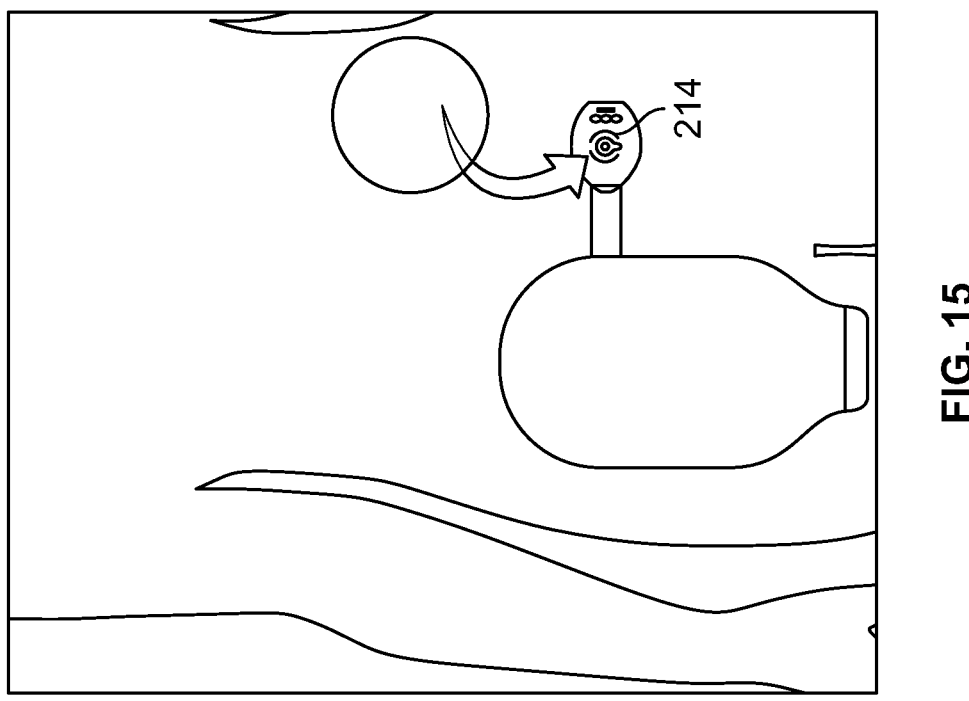
FIG. 15 is an illustration of a monitor device attached to user's body according to another embodiment.
Figure 14:
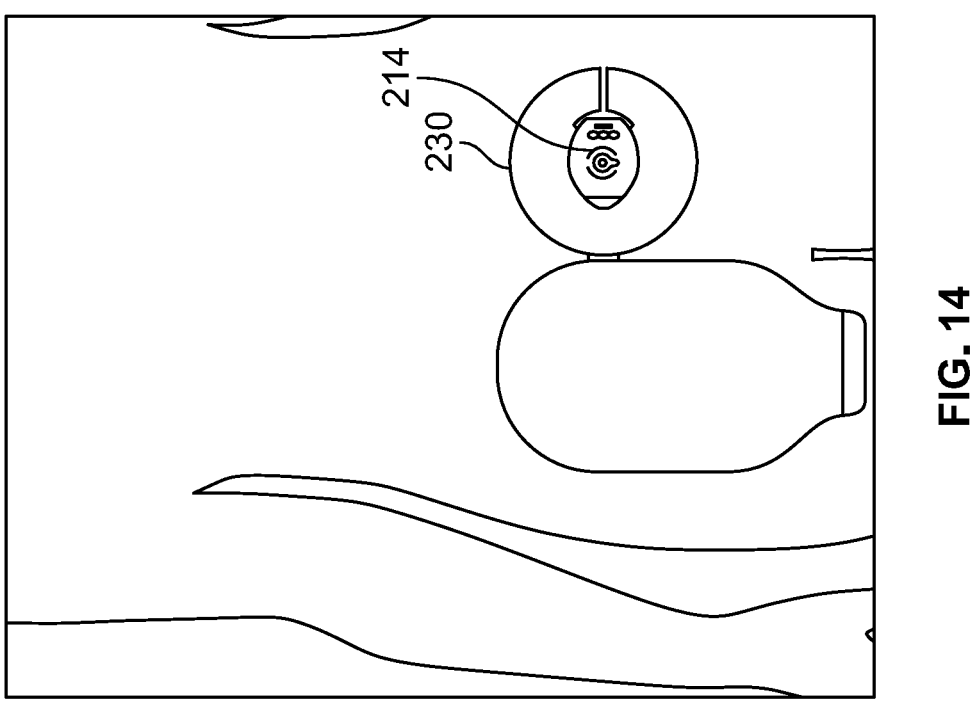
FIG. 14 is an illustration of a monitor device attached to user's body according to an embodiment.

In some embodiments, the monitor device may be attached to a user's body. In FIG. 14, a monitor device 214 may be coupled to a sensing accessory and attached to user's body via an attachment portion 214. In this embodiment, the attachment portion 214 may have a generally split ring-like shaped body, which may be integrally formed with the sensing accessory or provided as a separate member. In FIG. 15, the monitor device 214 may be coupled to a sensing accessory and attached to user's body using an adhesive pad provided on a body-side surface of the monitor device 214.

Referring back to FIGS. 2 and 3, the wearable subsystem 14 may comprise a hinged casing, an imbedded circuit board, a battery, a motor, and alignment members 40 that correspond to alignment members 36 of the sensing accessory 12. The circuit board may include conductive members 24 configured to contact terminal ends of sensing traces of the sensing accessory 12. In this embodiment, the conductive members 24 comprising a plurality of raised conductive pads may be arranged generally in a center area of a bottom housing of the wearable subsystem 14.

The alignment members 40 may comprise two raised members, each of which may be arranged on each side of the conductive members 24 as shown in FIG. 2. In such an embodiment, the alignment members 36 of the sensing accessory 12 may be defined by two openings, which may be configured to receive the raised alignment members 40 of the wearable subsystem 14. The alignment members 36, 40 may be configured to facilitate correct attachment of the wearable subsystem 14 to the sensing accessory 12 to ensure electrical connection therebetween. A user may form a connection between the sensing accessory 12 and the wearable subsystem 14 by aligning the corresponding alignment members 36, 40 as shown in FIG. 3 and closing the wearable subsystem 14.

Figures 16, 17, 18:
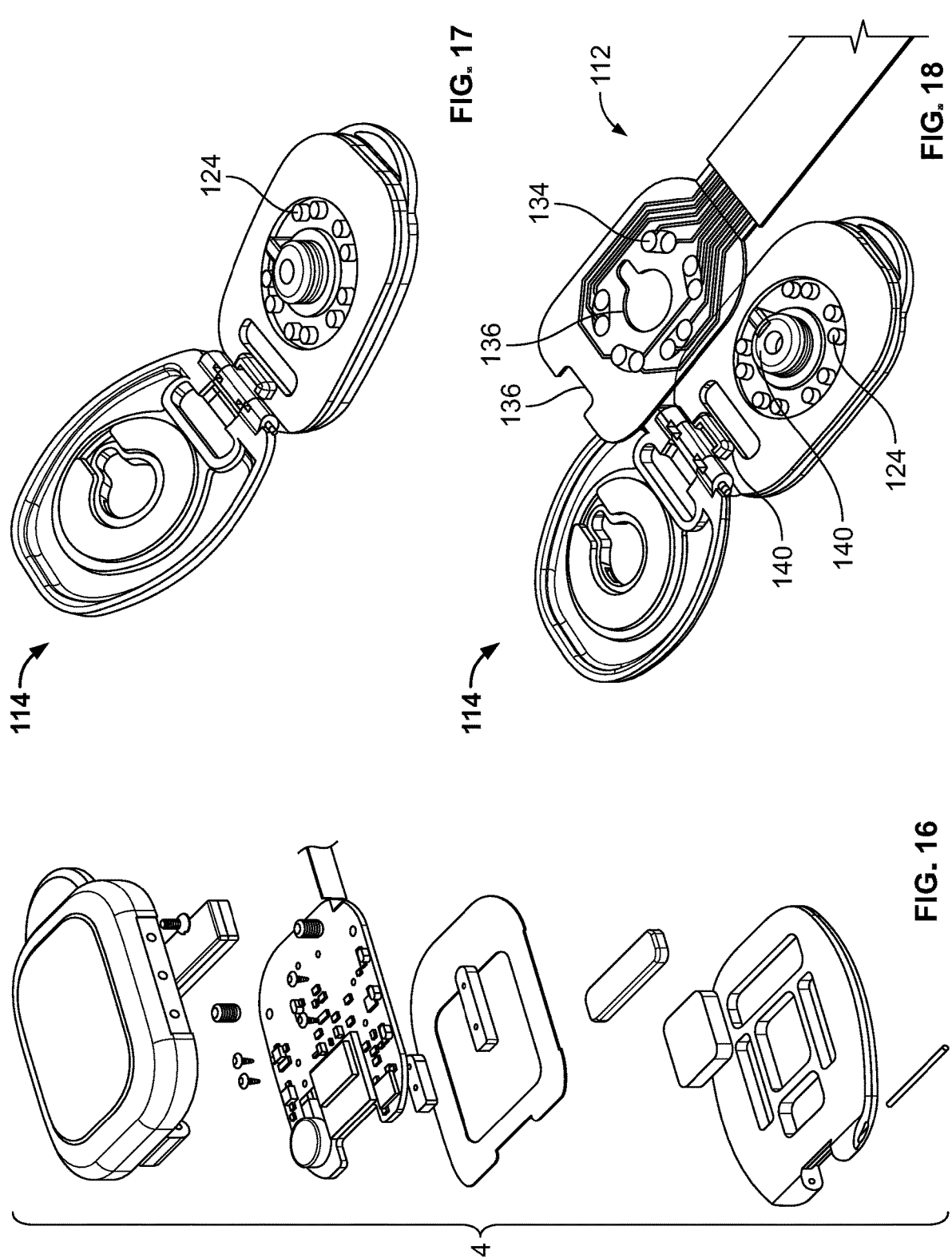
FIG. 16 is an exploded view of a monitor device according to an embodiment.
FIG. 17 is a perspective illustration of a monitor device according to an embodiment.
FIG. 18 is a perspective illustration of the monitor device of FIG. 17 and a connector region of a sensing accessory configured to engage the monitor device according to an embodiment.
Figures 23, 24:
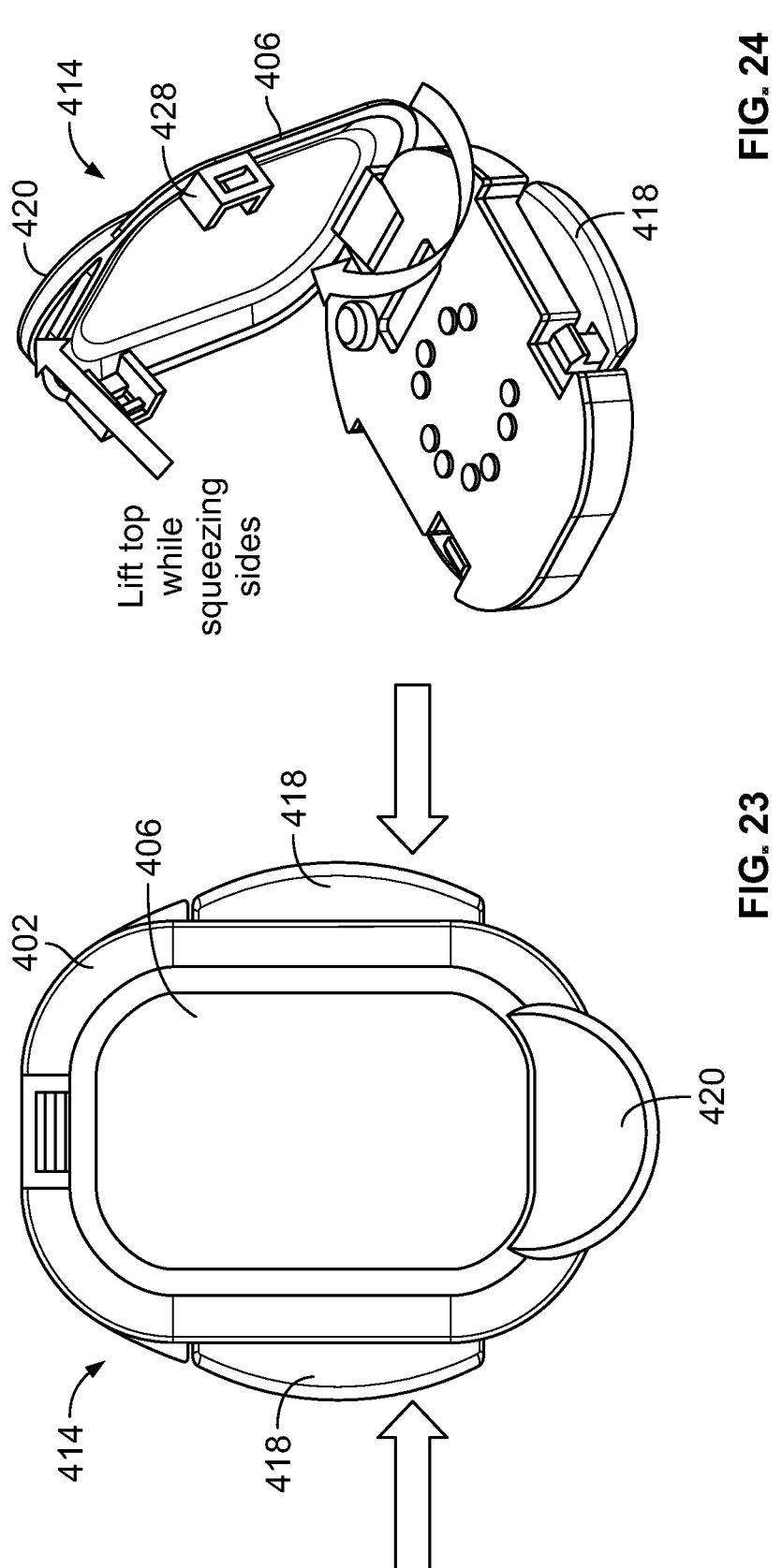
FIGS. 23-29 are various views of a monitor device according to an embodiment.

The circuit board of the wearable subsystem 14 may include a processor and other components to analyze signals received from the sensing accessory 12, communicate with external devices, such as a mobile device and a charging dock 16, and alert a user vis sound, vibration, LEDs, etc. to notify a system status. FIG. 16 is an exploded view of a wearable subsystem 14 according to an embodiment.

FIGS. 17 and 18 show a wearable subsystem 114 according to another embodiment. The wearable subsystem 114 may be configured similar to the wearable subsystem 14, generally comprising a hinged casing, an imbedded circuit board, a battery, a motor, and an alignment member 140 that correspond to an alignment member 136 of a sensing accessory 112. The circuit board may include conductive members 124 configured to contact connecting points 134 of the sensing accessory 112.

Referring back to FIGS. 2 and 3, the wearable subsystem 14 may comprise a hinged casing, an imbedded circuit board, a battery, a motor, and alignment members 40 that correspond to alignment members 36 of the sensing accessory 12. The circuit board may include conductive members 24 configured to contact terminal ends of sensing traces of the sensing accessory 12. In this embodiment, the conductive members 24 comprising a plurality of raised conductive pads may be arranged generally in a center area of a bottom housing of the wearable subsystem 14.

The alignment members 40 may comprise two raised members, each of which may be arranged on each side of the conductive members 24 as shown in FIG. 2. In such an embodiment, the alignment members 36 of the sensing accessory 12 may be defined by two openings, which may be configured to receive the raised alignment members 40 of the wearable subsystem 14. The alignment members 36, 40 may be configured to facilitate correct attachment of the wearable subsystem 14 to the sensing accessory 12 to ensure electrical connection therebetween. A user may form a connection between the sensing accessory 12 and the wearable subsystem 14 by aligning the corresponding alignment members 36, 40 as shown in FIG. 3 and closing the wearable subsystem 14.

Figures 35, 36, 37A, 37B:
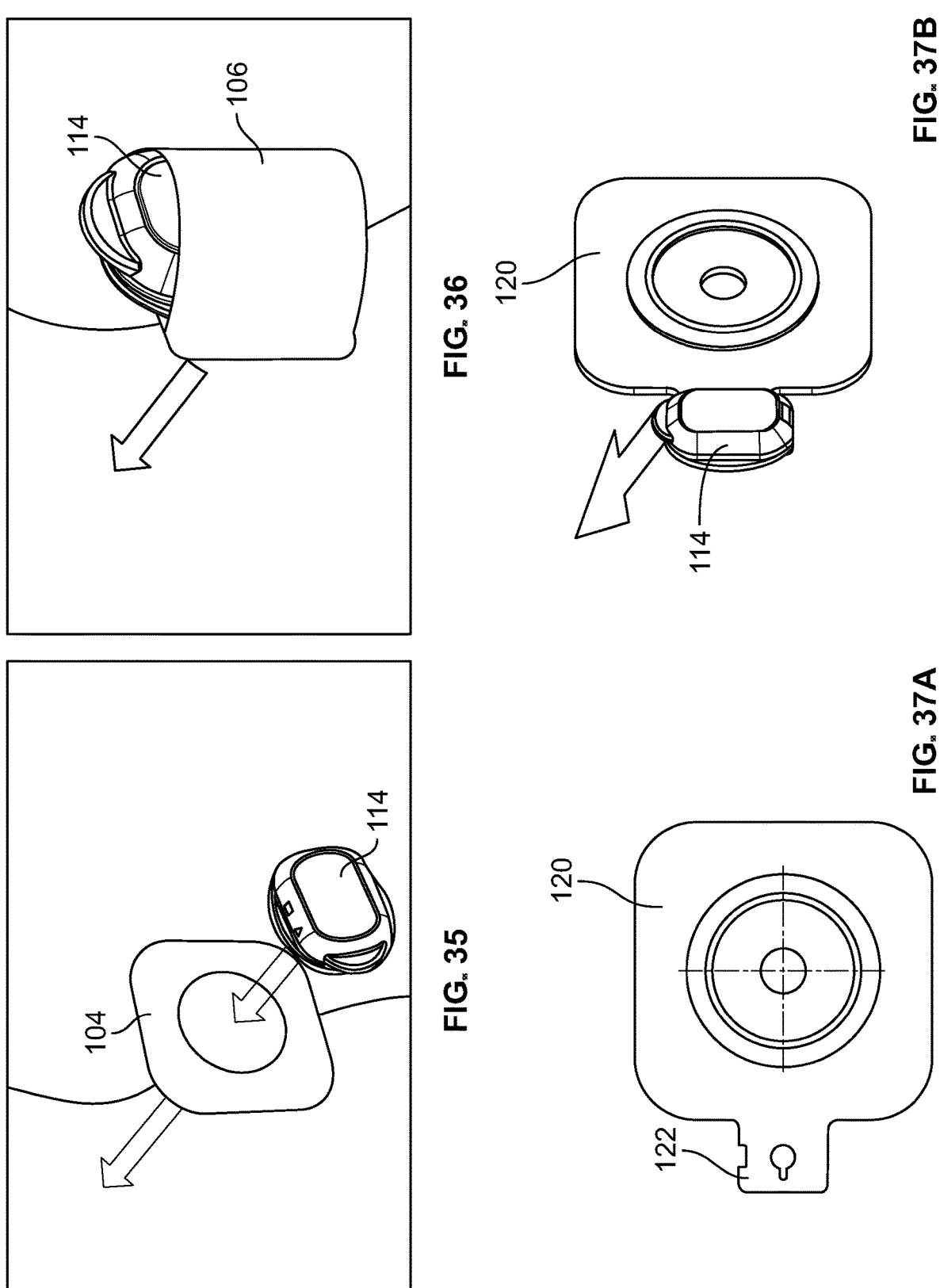
FIG. 35 is a perspective illustration of a monitor device and a double-sided adhesive patch for attaching the monitor device to a user or an ostomy pouch according to an embodiment.
FIG. 36 is a perspective illustration of a monitor device and a pocket for holding and attaching the monitor device to a user or an ostomy pouch according to an embodiment.
FIGS. 37A and 37B are perspective illustrations of an ostomy barrier including a tab for a monitor device attachment and a monitor device attached to the ostomy barrier.

In an embodiment, the wearable subsystem 114 may be attached to an ostomy pouch or user via an adhesive patch 102 as shown in FIGS. 19-22. In another embodiment, the wearable subsystem 114 may be mounted to an ostomy pouch or user via a double-sided adhesive patch 104 as shown in FIG. 35. The double-sided adhesive patch 104 may include an adhesive on both surfaces of the patch, wherein the wearable subsystem 114 may be attached to a distal side of the patch 104 and a body-side of the patch may be attached to a user or an ostomy pouch. Alternatively, the patch 104 may include other types of fasteners, such as hook and loop fasteners, for attaching the wearable subsystem 114 to a user or an ostomy pouch.

FIG. 36 shows a pocket 106 configured to hold the wearable subsystem 114 according to an embodiment. The pocket 106 may be provided with an adhesive or other fasteners for attaching the pocket 106 to a user or an ostomy pouch. FIG. 37A shows an ostomy barrier 120 including a tab 122 for attachment of the wearable subsystem 114 according to an embodiment. FIG. 37B shows the ostomy barrier 120 with the wearable subsystem 114 attached to the tab 122.

Figure 25:
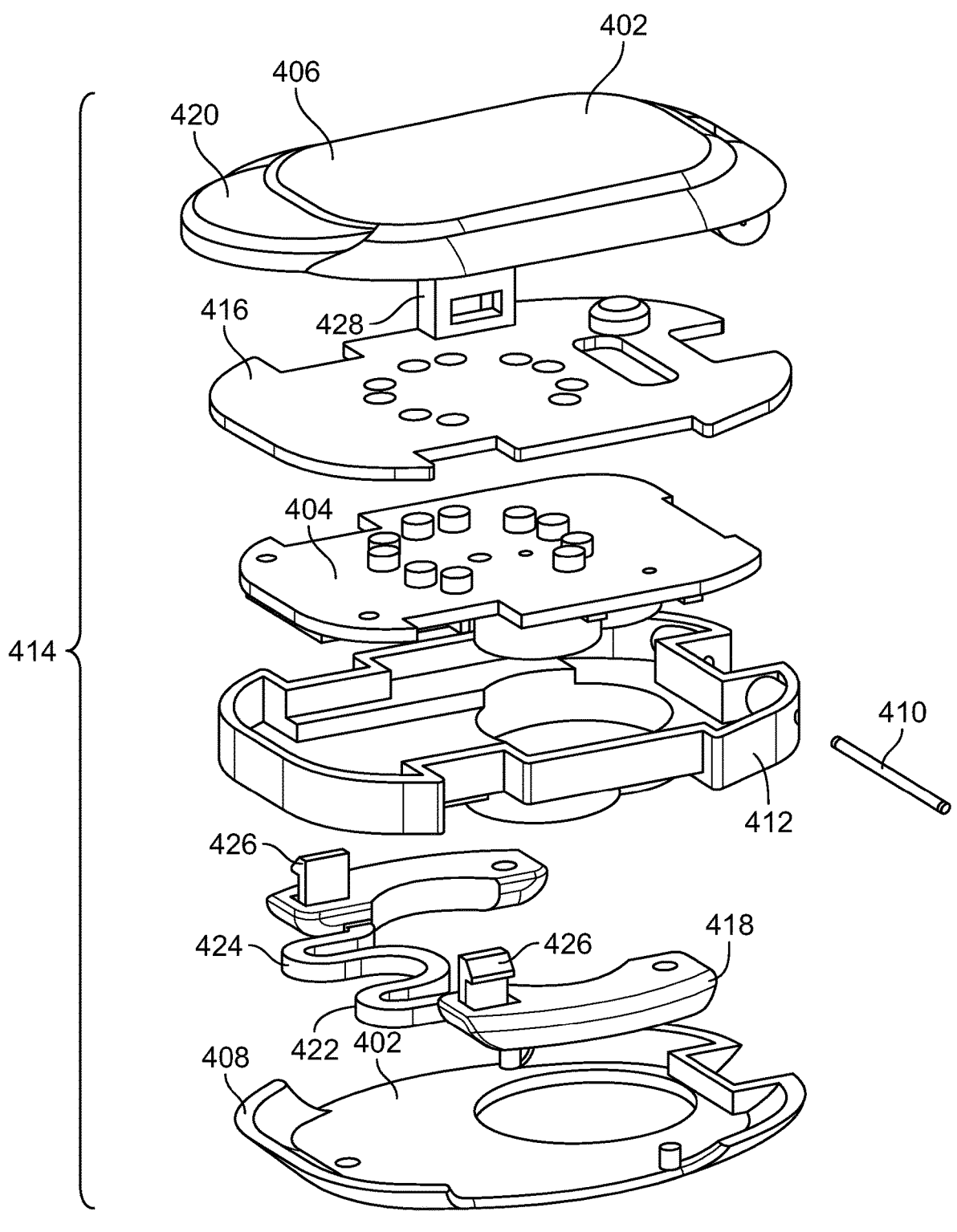

FIGS. 23-29 show a monitor device 414 according to an embodiment. The monitor device 414 may be configured similar to the monitor device 14, 114, generally comprising electronics 404 contained in a hinged casing 402. The hinged casing 402 may include a top casing 406 and a bottom casing 408 connected via a hinge pin 410. As best shown in FIG. 25, the electronics 404 may be arranged in an electronics housing 412 and covered with a board seal 416 configured to protect the electronics 404 from humidity and external environment.

The monitor device 414 may be configured to be opened by squeezing side claps 418 and lifting a top clasp 420. In this embodiment, the monitor device 414 may include a squeeze release device 422 comprising the side claps 418 connected by a spring 424 and a pair of latches 426, which may be configured to engage a pair of catches 428 provided on the top casing 406. The monitor device 414 may be configured such that the pair of latches 426 are engaged with the pair of catches 428 when closed. To open the monitor device 414, a user may squeeze the side claps 418 in the direction indicated by the arrows in FIG. 23 to release the latches 426 and lift the top clasp 420 as indicated by the arrows in FIG. 24.

Figures 26, 27, 28, 29:
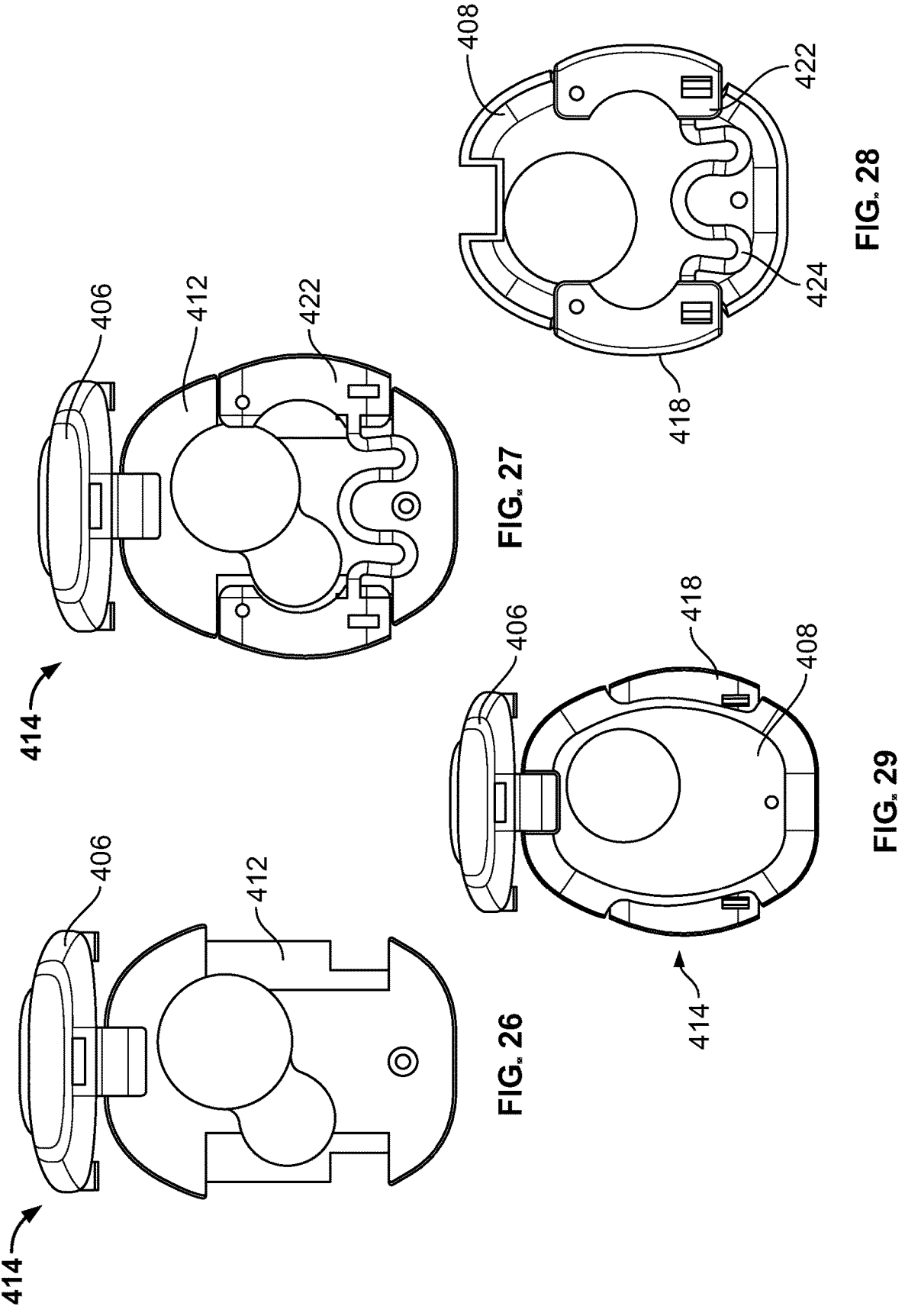

In an embodiment, the squeeze release device 422 may be formed as a single injection molded piece. The squeeze release device 422 may be arranged in the bottom casing 408, and the electronics housing 412 containing the electronics 404 may be arranged over the squeeze release device 422. FIG. 26 shows a bottom view of the monitor device 414 without the bottom casing 408 and the squeeze release device 422 to illustrate a bottom view of the electronic housing 412. FIG. 27 shows a bottom view of the monitor device 414 without the bottom casing 408 to illustrate a bottom view of the electronics housing 412 arranged over the squeeze release device 422. FIG. 28 is a top view of the squeeze release device 422 placed in the bottom casing 408. FIG. 29 is a bottom view of the monitor device 414.

Figures 30, 31:
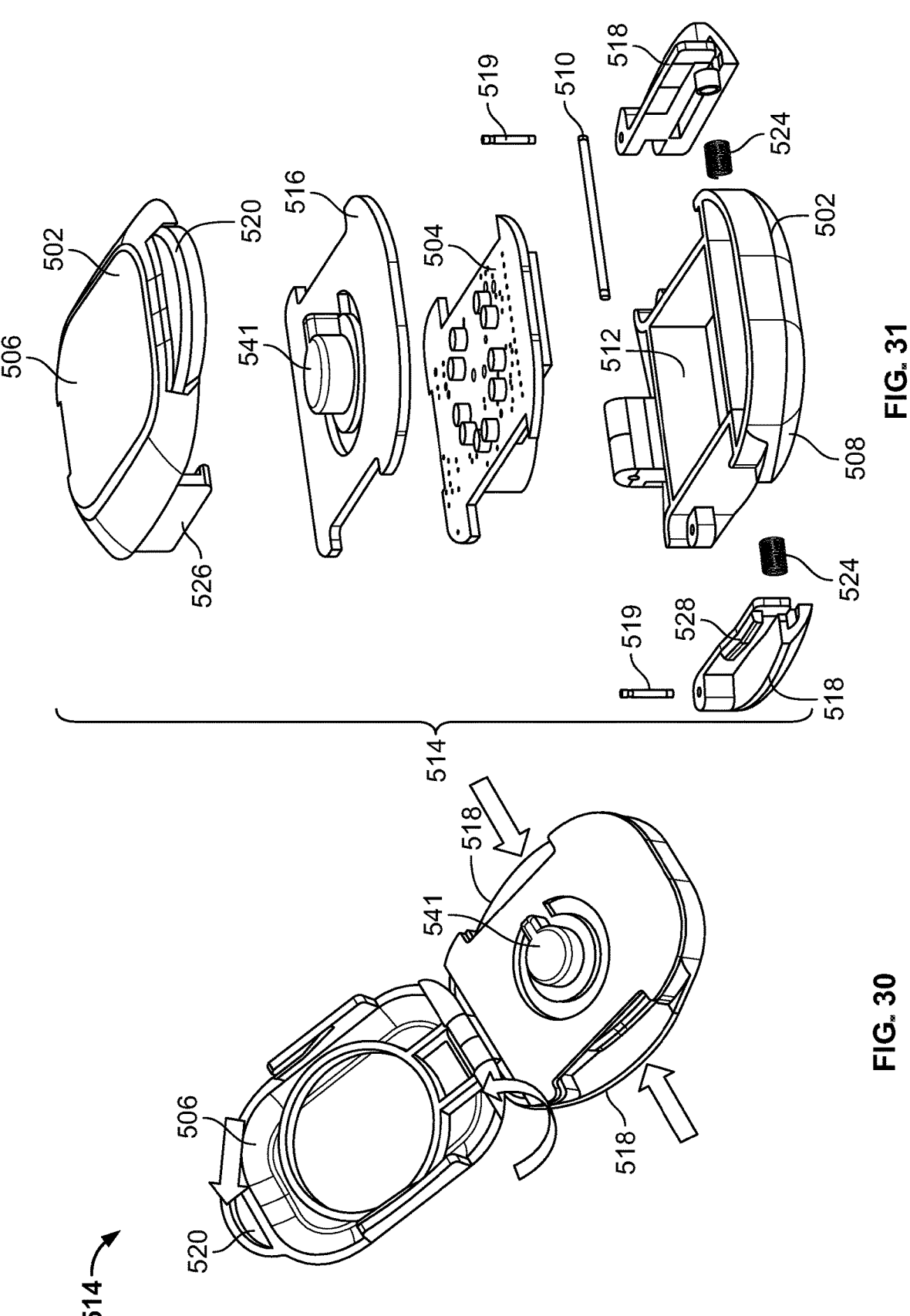

FIGS. 30-34 show a monitor device 514 according to an embodiment. The monitor device 514 may be configured similar to the monitor device 414 generally comprising electronics 504 contained in a hinged casing 502. The hinged casing 502 may include a top casing 506 and a bottom casing 508 connected via a hinge pin 510. In this embodiment, the bottom casing 508 may include a chamber 512 configured to contain the electronics 504. The monitor device 514 may also include a board seal 516 configured to cover and protect the electronics 504 from humidity and external environment. The board seal 516 may include a raised key member 541 for facilitating alignment of a sensing accessory. FIG. 30 is a perspective top view of the monitor device 514 in an open position. FIG. 31 is an exploded view of the monitor device 514. FIG. 32 is a cross-sectional view of the monitor device 514, and FIG. 33 is a bottom view of the monitor device 514. FIG. 34 is a perspective top view of the monitor device 514 in an open position excluding electronics 504 and the board seal 516.

The monitor device 514 may be configured to be opened by squeezing side claps 518 and lifting a top clasp 520 as indicated by the arrows in FIG. 30. In this embodiment, the top casing 506 may be integrally formed with a pair of latches 526. Each of the side claps 518 may be provided with a catch 528 configured to engage with the latch 526. The side claps 518 may be attached to the bottom casing 508 via hinge pins 519. A spring 524 may be provided between each of the side claps 518 and the bottom casing 508, such that the side claps 518 may be squeezed toward the bottom casing 508. The monitor device 514 may be configured such that the pair of latches 526 are engaged with the pair of catches 528 in a closed position as shown in FIG. 32. To open the monitor device 514, a user may squeeze the side claps 518 to release the latches 526 and lift the top clasp 520 as shown in FIG. 30.

During use, the wearable subsystem may poll resistance measurements from conductive traces to collect resistance data, which may be processed through an algorithm for determining an ostomy effluent leakage event. The algorithm may consider resistance measurements and other factors, such as resistance measurements from neighboring conductive traces, a change in resistance from recent prior resistance measurements, historical data from prior uses, etc.

Upon a detection of an ostomy effluent leakage event, the wearable subsystem may alert a user via sound, vibration, light, etc. according the leakage event. An alert may be sent based on resistance measurements received from multiple sensors, patterns in measurements, user preference inputs, signals received from other components of the ostomy leakage detection system, such as a mobile application and/or charging dock.

The wearable subsystem may be configured to communicate data to a mobile application. The data may be raw sensor data as received from the sensing accessory or processed data processed by the wearable subsystem which may include a summarized data and/or a leakage event information. The wearable subsystem may also be configured to communicate system conditions, such as the connectivity of the sensing accessory a faulty sensor, a state of battery, etc. The wearable subsystem may be powered by a battery or recharged by the charging dock 16. The wearable subsystem may include conductive pads on a charge circuit portion of the circuit board, which may be configured to contact pins on the charging dock.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular. In additions, various features described with respect to any of the embodiments above may be used together, implemented in, or replace features in any of the other embodiments described above.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. An ostomy leakage detection system comprising:
   a sensing accessory comprising sensors configured to detect ostomy effluent leakage under a skin barrier of an ostomy pouch system, wherein the sensing accessory includes a sensor portion configured to be attached to the skin barrier and an attachment portion; and
   a monitor device configured to communicate with the sensing accessory to receive ostomy effluent leakage data;
   wherein the monitor device is configured to engage with the sensing accessory and the attachment portion is configured to secure the monitor device to the ostomy pouch system or to a user's body.

2. The ostomy leakage detection system of claim 1, wherein the monitor device is attached to a body-side surface of the ostomy pouch system or a distal surface of the ostomy pouch system.

3. The ostomy leakage detection system of claim 1, wherein the sensing accessory includes a first alignment member and the monitor device includes a second alignment member, wherein the sensing accessory and the monitor device are engaged with each other by aligning the first and second alignment members.

4. The ostomy leakage detection system of claim 1, wherein the attachment portion comprises an adhesive.

5. The ostomy leakage detection system of claim 1, wherein the attachment portion comprises a hook member or a loop member, wherein the monitor device is attached to the ostomy pouch system by engaging the hook member or the loop member of the attachment portion to a corresponding hook or loop member provided on the ostomy pouch system.

6. The ostomy leakage detection system of claim 4, wherein the monitor device is releasably coupled to the sensing accessory, such that the monitor device can be removed after the attachment portion is attached to the ostomy pouch system.

7. The ostomy leakage detection system of claim 1, wherein the monitor device is magnetically clipped to the ostomy pouch system.

8. The ostomy leakage detection system of claim 1, wherein the monitor device is attached to the ostomy pouch system or user's body via an adhesive patch separately provided from the monitor device.

9. The ostomy leakage detection system of claim 1, wherein the monitor device is attached to the ostomy pouch system or user's body via a pocket configured to hold the monitor device.

\* \* \* \* \*